United States Patent [19]

Hafele et al.

[11] Patent Number: 6,055,847

[45] Date of Patent: *May 2, 2000

[54] MEASURING SENSOR HAVING METAL JACKET LEAD AND EXTERNALLY MOUNTED THREADED CONNECTOR

[75] Inventors: Edelbert Hafele, Karlsruhe; Walter Seeger, Gaggenau, both of Germany

[73] Assignee: Heraeus Holding GmbH, Hanau, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/972,538

[22] Filed: Nov. 18, 1997

Related U.S. Application Data

[63] Continuation of application No. 08/669,361, filed as application No. PCT/EP95/00042, Jan. 5, 1995, abandoned.

[30] Foreign Application Priority Data

May 1, 1994 [DE] Germany ............................ 44 00 220

[51] Int. Cl.[7] .................................................. G01D 11/24
[52] U.S. Cl. ...................... 73/31.05; 73/31.06; 73/866.5; 338/34; 204/424
[58] Field of Search ............................... 73/23.31, 31.05, 73/31.06, 863.51, 803.85, 866.5; 338/34, 233, 273, 274, 317; 204/424, 426; 174/100 P, 105 R

[56] References Cited

U.S. PATENT DOCUMENTS

| 2,523,691 | 9/1950 | Fitch . | |
|---|---|---|---|
| 3,824,368 | 7/1974 | Locke . | |
| 4,033,169 | 7/1977 | Fujishiro et al. | 73/23.31 |

(List continued on next page.)

FOREIGN PATENT DOCUMENTS

| 0015062 | 9/1980 | European Pat. Off. . |
|---|---|---|
| 2707062 | 9/1977 | Germany . |
| 2702578 | 7/1978 | Germany . |
| 4015486 | 11/1990 | Germany . |
| 9208127 | 5/1992 | WIPO . |

OTHER PUBLICATIONS

Balzers—Vakuumtechnik, Catalogue of 1993, "Fluesigkeitsdurchfuehrung" (Penetration for Liquids, p. 26, "Elektrische Durchfuehrung" (Bushing for Electrical Cables), p. L 28.

Laszlo Kortvelyessy, "Thermoelement Praxis" [Thermoelements—in Practice], Vulkan–Verlag Essen, 1981, p. 228, ILL 2.53.

Patent Abstracts of Japan, vol. 12, No. 2 (P–652) Jan. 7, 1988 & JP A 62 163 961 Fujikura Ltd Jul. 20, 1987—abstract.

*Primary Examiner*—Daniel S. Larkin
*Assistant Examiner*—Michael Cygan
*Attorney, Agent, or Firm*—Antonelli, Terry, Stout & Kraus, LLP

[57] ABSTRACT

A measuring sensor for measuring a fluid includes a longitudinally extending housing having first and second ends and having an inlet opening at the first end for the fluid to be measured, and a sensor chip provided in the housing. The sensor chip has a sensor element provided towards the inlet opening and at least one electrically conducting contact provided towards the second end of the housing. The electrically conducting contact is connected to the exterior by a metal jacket lead having an outer metal tube, at least one internal conductor, and a mineral material for electrically insulating the at least one conductor, the outer metal tubing connected in a fluid-tight manner to the second end of the housing. In order to secure the sensor to an installation opening, a collar is welded to an outside of the housing at a selected position corresponding to a selected installation depth of the opening of the housing into the measuring opening. A threaded connector is provided over the collar such that the thread connector mates with a correspondingly threaded element of the measuring opening and secures the sensor in the measuring opening with the selected installation depth by bearing against the collar.

3 Claims, 4 Drawing Sheets

U.S. PATENT DOCUMENTS

| | | |
|---|---|---|
| 4,058,789 | 11/1977 | Bavisotto . |
| 4,193,965 | 3/1980 | Cullingford . |
| 4,230,930 | 10/1980 | Chang . |
| 4,308,518 | 12/1981 | Hattori et al. ............................ 73/23.31 |
| 4,437,914 | 3/1984 | Frischen ................................. 156/54 |
| 4,512,827 | 4/1985 | Gill ........................................ 156/48 |
| 4,569,817 | 2/1986 | Underwood . |
| 4,622,455 | 11/1986 | Schwarzkopf . |
| 4,669,321 | 6/1987 | Meyer ................................... 73/863.85 |
| 4,689,443 | 8/1987 | Bailleul ............................... 174/102 P |
| 4,742,717 | 5/1988 | Ichino .................................... 73/866.5 |
| 4,750,062 | 6/1988 | Wertheimer . |
| 4,883,643 | 11/1989 | Nishio . |
| 5,017,340 | 5/1991 | Pribat . |
| 5,329,806 | 7/1994 | McClanahan et al. ................. 73/31.05 |
| 5,536,478 | 7/1996 | Lipp et al. .............................. 422/174 |

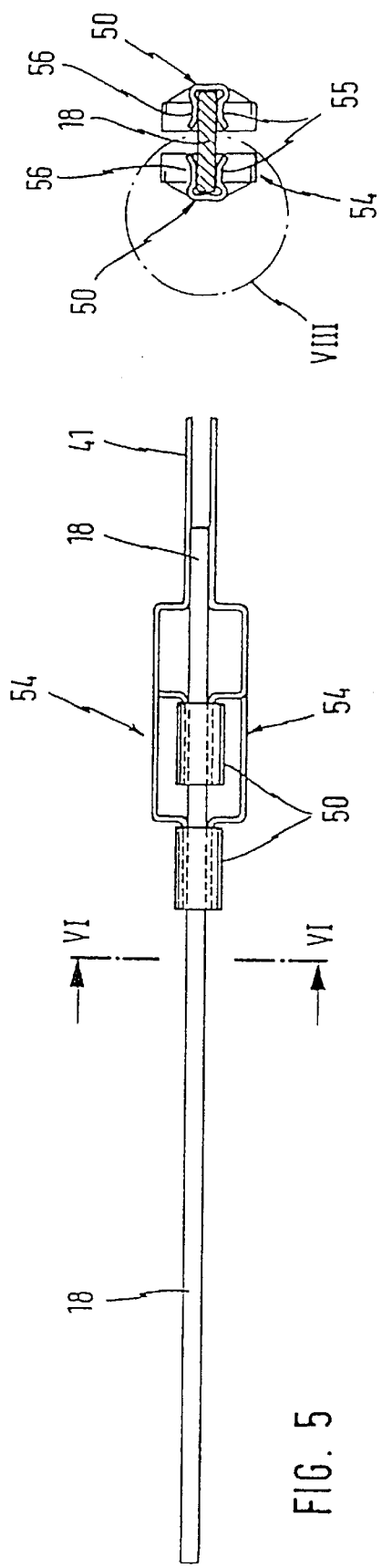
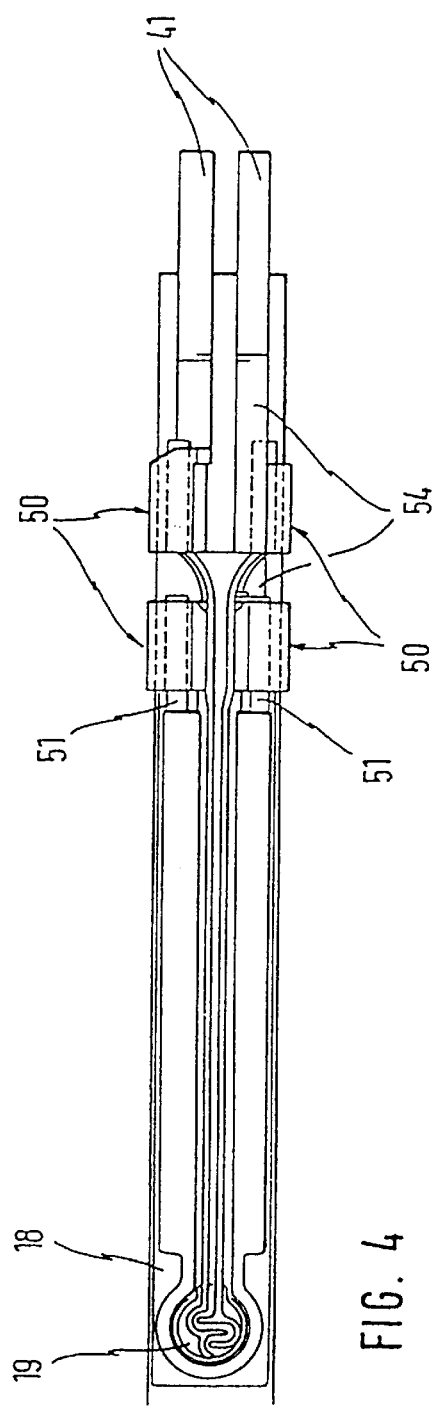
FIG. 4
FIG. 5
FIG. 6

MEASURING SENSOR HAVING METAL JACKET LEAD AND EXTERNALLY MOUNTED THREADED CONNECTOR

This is a continuation of application Ser. No. 08/669,361, filed Aug. 28, 1996, now abandoned, which is a 371 of PCT International Application No. PCT/EP95/00042, filed Jan. 5, 1995.

BACKGROUND OF THE INVENTION

Measuring sensors of this kind are known for example as lambda sensors in a plurality of embodiments. All sensors suffer from the problem that firstly they must have an opening through which the gas to be measured can enter and reach the sensor chip itself, and secondly they must be made gas-tight in order to prevent the measured gas from escaping at the place where the measuring sensor is preferably screwed in place. In particular however, the mechanical mounting of the sensor chip in the hot and pulsating exhaust of internal combustion engines and the thermal loadability of the electrical connection pose problems.

SUMMARY OF THE INVENTION

Hence, the goal of the invention is to design a measuring sensor according to the species in a simple fashion with sufficient mechanical as well as thermal loadability.

This goal is achieved in a measuring sensor according to the species.

The measuring sensor is therefore disposed according to the teaching of the invention in a housing in which the electrical and mechanical connection of the sensor chip, which contains a ceramic, preferably $Al_2O_3$, is performed by direct or indirect laser welding to the trace or traces of the sensor chip.

The measuring sensor itself, according to the teaching of the invention, can be located in a cylindrical or metallic housing into which the electrical connection, in the form of an internal conductor surrounded by a metal jacket tube, hereinafter referred to as the metal jacket lead for short, is introduced, the metal jacket of said lead being connected directly or indirectly with the metal housing by welding or soldering. Preferably, the metal jacket lead is introduced into the tubular housing from one end, into the tube which is open at that location. The internal electrical conductor in the metal jacket lead can be embedded in an electrical insulator, MgO for example, inside the metal jacket tube. The metal jacket tube provides an absolutely gas-tight feedthrough for the electrical connecting wires from the housing. In this design, the sensor chip can also be secured purely mechanically at one end by the more or less rigidly acting internal conductor of the metal jacket lead, directly or indirectly. An appropriate choice of material for the internal conductor, for example an alloy containing copper and/or aluminum and/or iron and/or nickel and/or chromium, also ensures high thermal loadability.

According to one especially preferred embodiment, the electrical connection has a clip that is pushed laterally in a mechanically clamping fashion onto both the top and bottom of the sensor chip, over its edge on the long side of the sensor chip that is made plane, and rests firmly and with zero play on the contact trace. The clip is laser-welded to the contact trace of the sensor chip, which preferably consists of a noble metal, platinum for example, and is mounted on the substrate of the sensor chip by means of an adhesion promoter. The adhesion promoter preferably contains the same noble metal as the contact trace, as well as glass and/or ceramic components. The clip also has a contact tab extending toward the insertion opening, said tab being bent into the shape of a U for the purpose of thermal length compensation and also being in the form of a strip. One of the connecting wires of the internal conductor is connected to the connecting tab, also preferably by laser welding. As a result of the U-shaped bend, an additional clip can be placed in the area between the two legs of the U on another contact trace of the sensor chip, so that four clips can be applied without difficulty.

In an open system (FIG. 3) the electrical connecting wires of the internal conductor which are brought out from the metal jacket lead can be exposed directly to the hot exhaust, from an internal combustion engine for example, and must therefore consist either of surface-refined lead wires or solid oxidation-resistant materials. Preferably, however, a half-open system is used in the invention (FIGS. 1 and 2), in which a supporting element that supports the chip additionally is provided between the electrical connecting wires and the actual part of the sensor chip that bears the sensor element. In addition, the supporting element, when it is in the form of a pre-shaped wire knit, can also capture particles of dirt or the like that are present in the gas, so that they cannot reach the vicinity of the insertion opening.

In another embodiment of the invention, the electrical connecting wires can be guided in an arc from the metal jacket lead to the sensor chip itself and can thus compensate for tensile forces and equalize thermal expansion. Depending on the length of the electrical leads, they can also have a highly conductive core, made of copper or silver for example. The connecting wires can be attached for example by direct contact of these wires (possibly with previous shaping and also with shaping of the arc) with the contact trace of the sensor chip, but also can be connected by means of a connecting sleeve. Direct contact with the substrate is always produced by laser welding. In all other contacts, for example indirect (including non-electrical) contacts, on the other hand, other welding methods may be used. The connecting sleeve is guided over the connecting tab and over the ends of the electrical connecting wires, and can likewise consist of a high-temperature-resistant and corrosion-proof material. The oxidation-prone open ends of the two connecting wires are tightly sealed by the subsequent welding. Corrosion of the open ends of the connecting lead can likewise be suppressed by the protective sleeve of the wire core being machined to overlap and fit snugly, resulting in gas-tightness. In the prior art, the sensor chip itself is always connected to the electrical connection and the sensor element is always mounted in the vicinity of a part of the housing that is already separated in a gas-tight manner, so that considerable expense may be involved in sealing.

In addition, the sensor chip can be metallized on one side for improved handling during the manufacturing process, to which metallization one or more small feet of small legs of a retaining part can be welded, said metallization generally being connected by a link with the metal jacket tube introduced into the interior of the housing of the measuring sensor, preferably by welding. Thus, even during the manufacturing process, there is a certain stability of the individual parts to be connected together. In addition, there is a definite anchor for the sensor chip itself. An increase in the length of the sensor chip as a result of thermal expansion beyond the length that is in contact can be compensated by this type of small leg of the retaining part that runs at right angles to the length of the sensor chip by virtue of the fact that the small legs can pivot through a small angle. The different expansions over the length of the contact between the sensor chip and the retaining part are mechanically relieved from the standpoint of thermal stress by the small legs.

The small legs in this case are mounted on one end of the sensor chip. The other end can also be held in place by a connection having one or more small legs, with the small feet provided at the ends of the small legs pointing away at right angles from the sensor chip itself and then being directed at right angles once more along the length of the tubular housing of the measuring sensor. By means of a resultant V-shaped bend, permanently welded at its free end to the inside of the housing, firstly a secure mounting of the sensor chip itself is obtained and secondly the V-shaped design permits safe thermal expansion without damage to the sensor chip. Both mounts are also preferably made of a high-temperature-resistant as well as corrosion-resistant material, for example the same material as the housing of the sensor chip. Both areas of the mechanical mount abutting the small feet are located at a distance from the interior of the tubular metal housing of the measuring sensor. In general, this results in a good mechanical connection firstly to the sensor chip itself and secondly to the metal housing of the measuring sensor. Moreover, if the same materials are used, an identical thermal coefficient of expansion advantageously results. Finally, it is possible for the small feet not only to be located on one side of the sensor chip itself but also to fit around its edge at least partially and/or partially engage or fit into or over recesses in the vicinity of the edge of the sensor chip, so that a firm mechanical mount is achieved by virtue of an additional positive or nonpositive fit.

The fact that practically all the individual parts to be connected with one another can be joined by laser welding is especially advantageous.

In open as well as half-open systems, the response time of the sensor can be adjusted by additionally providing openings on the circumference of the anterior area of the housing. In addition, the anterior holder of the sensor chip in the open version can be designed simultaneously as a mechanical protection for the sensor element. By changing the position of the collar mounted on the housing as a counterbearing for a union nut, the installation depth of the measuring sensor can be varied in a very simple fashion.

In summary then, it is clear that in the preferred embodiment both the electrical and mechanical connections of the sensor chip are made by the clips that rest flush on its contact traces and are connected in this area by laser welding, with the connecting wires of the internal conductor of the metal jacket lead likewise being welded to the connecting tabs of said clips, resulting in an especially simple and logical solution.

BRIEF DESCRIPTION OF THE DRAWINGS

Embodiments of the invention will now be described in greater detail with reference to the drawing.

FIG. 4 is a third embodiment of the invention in a top view.

FIG. 5 shows the embodiment in FIG. 4 in a side view;

FIG. 6 is a section VI—VI according to FIG. 5;

DETAILED DESCRIPTION OF THE PREFERRED EMBODIMENTS

Figure 1:
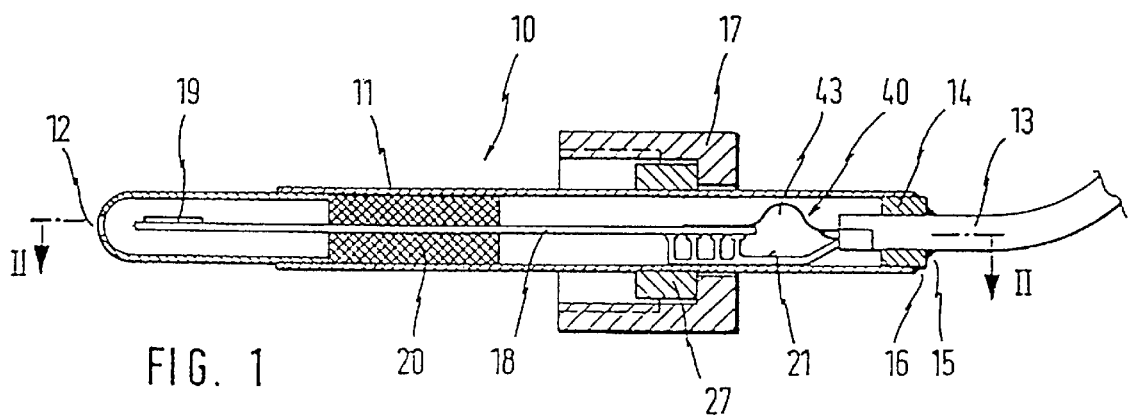
FIG. 1 shows a schematic cross section through a first embodiment of the measuring sensor.
Figure 2:
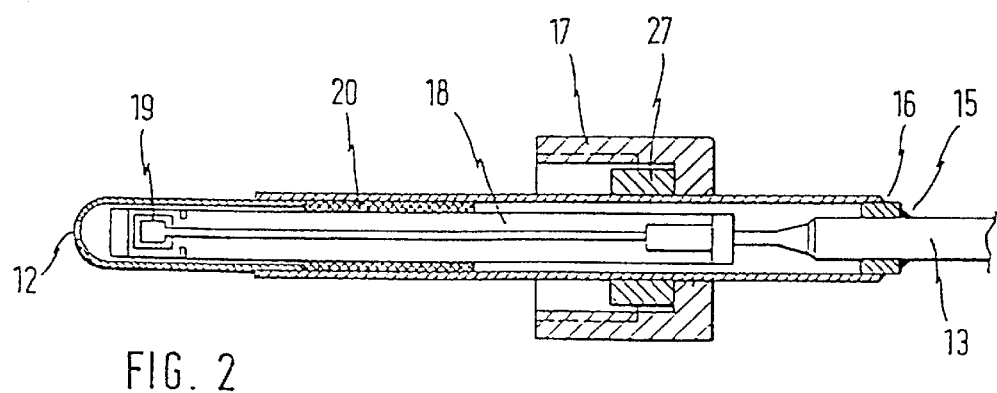
FIG. 2 is a section II—II according to FIG. 1.

The first embodiment (FIGS. 1 and 2) of a measuring sensor, designated as a whole by 10 in FIG. 1, has a housing designed as a cylindrical tube 11 made of a metallic material, one of whose sides, facing the gas to be measured, has an open end with an inlet opening 12 and at the other end has an electrical connection 13 designed as a metal jacket lead, said lead 13 being provided with a mounted bushing 14 firstly connected with the outer tube of the metal jacket lead by means of a laser-welded connection 15 and by means of a weld 16 with the open end of tube 11.

A union nut 17 is provided in the central area, said nut serving to screw the entire measuring sensor into a measuring opening over a collar 27 that serves as a counterbearing, said collar likewise being connected with tube 11 by welding.

The actual sensor element 19 of sensor chip 18, which extends in the lengthwise direction of the tube, is located at the forward end of tube 11, in its area facing inlet opening 12. Between the actual sensor element 19 and the end of the sensor chip 18 on the connecting side, a supporting support part 20, made of a correspondingly shaped and/or preshaped wire knit, is pushed onto it. As a result, the sensor chip is firstly held mechanically in its area facing inlet opening 12, the mechanical hold being at right angles to the length of the tube. On the other hand, particles and the like contained in the exhaust cannot penetrate to the vicinity of the electrical connection of the metal jacket lead 13.

Figure 7:
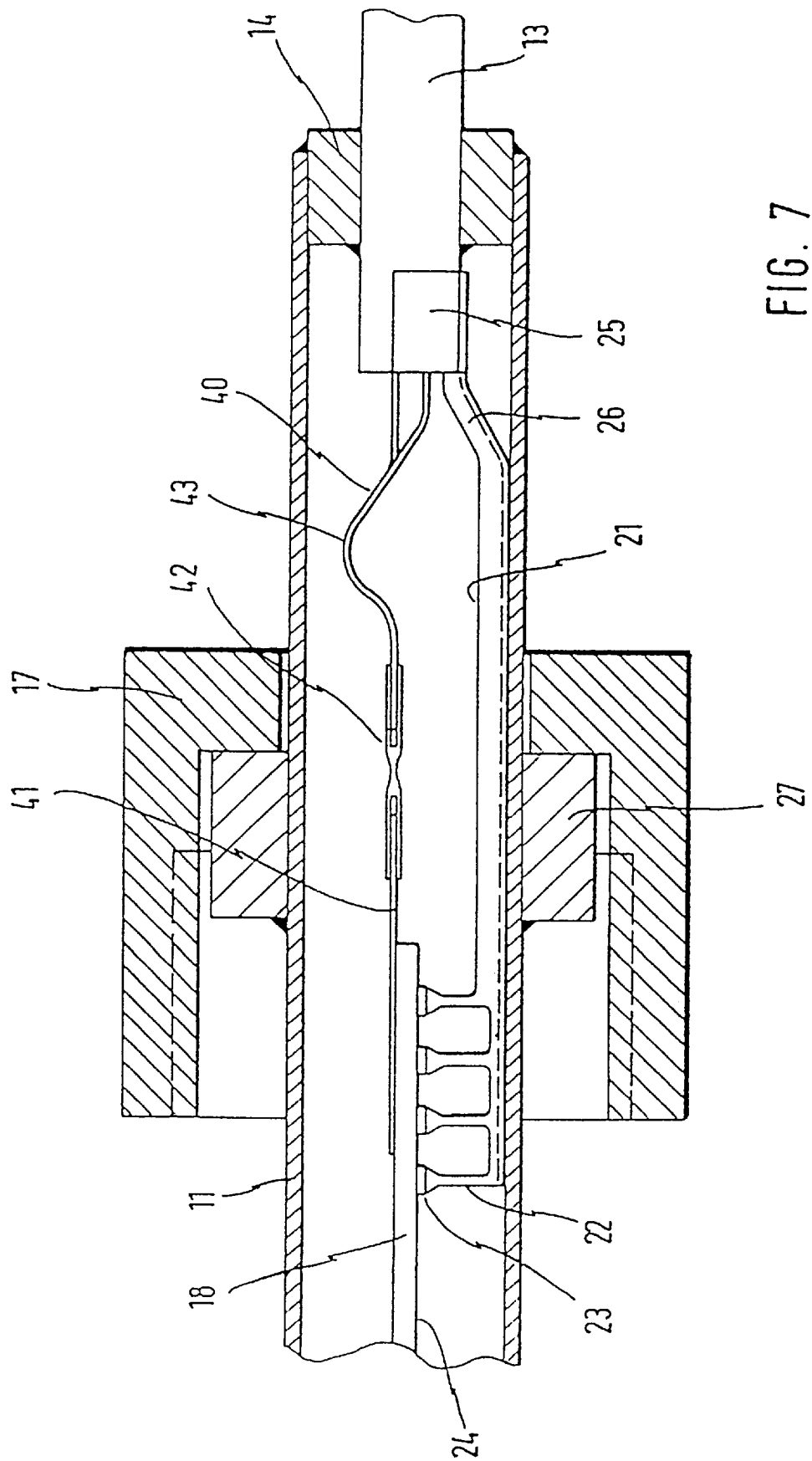
FIG. 7 shows detail VII according to FIG. 3.
Figure 8:
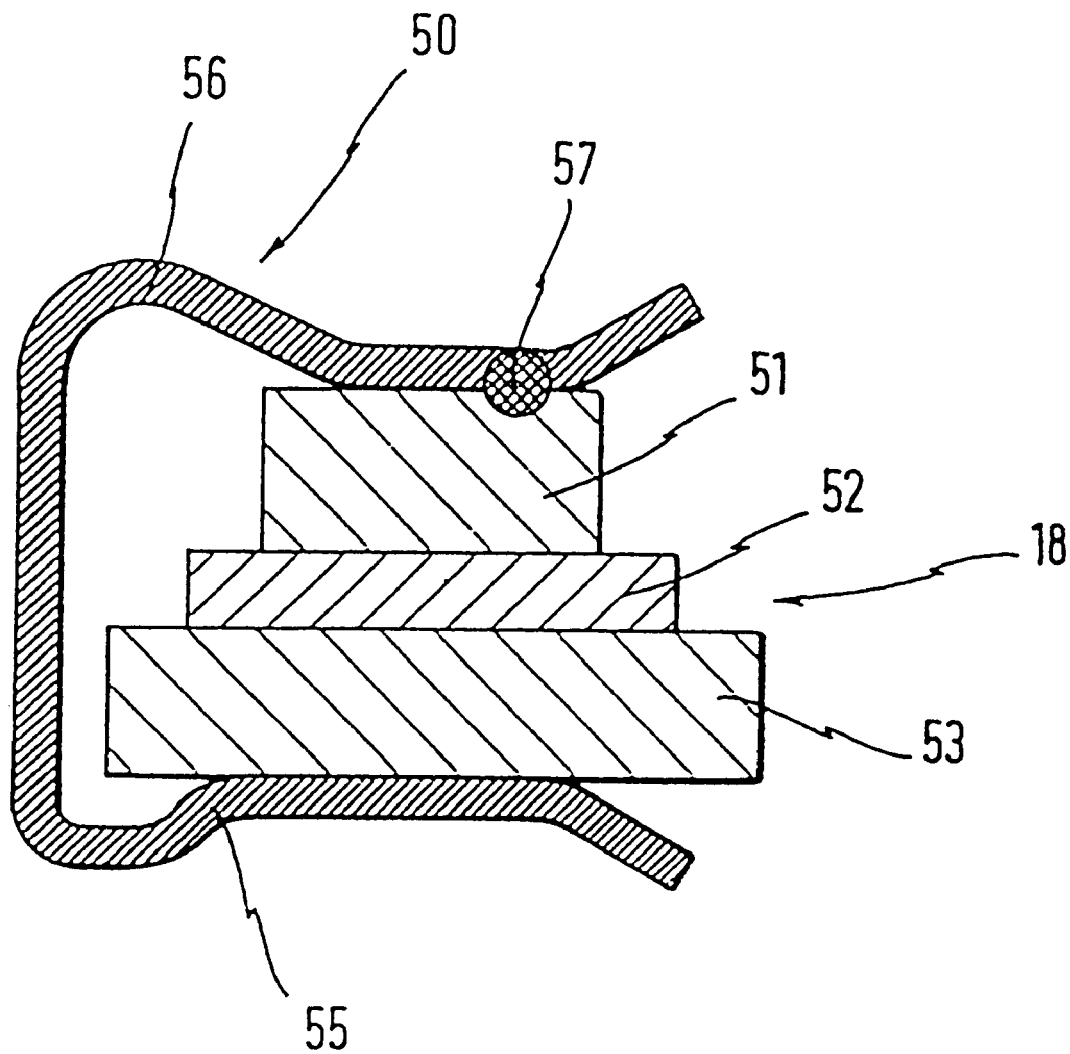
FIG. 8 shows detail VIII according to FIG. 6, schematically and on an enlarged scale.

In the first (FIGS. 1 and 2) and second (FIGS. 3 and 7) embodiment, a holding part is provided in the area of sensor chip 18 facing away from actual sensor element 19 and is designated as a whole by 21. This holding part runs essentially parallel to the length of tube 11. Small legs 22 project from it at right angles, said legs being provided at their ends with small feet 23 (FIG. 7). The side of sensor chip 18 at the bottom in FIG. 7 has a metallization designated as a whole by 24, to which small feet 23 of the holder designated as a whole by 21 are welded. In addition, holding part 21 can also be connected by welding or soldering with a surrounding piece 25 bent around a bend 26 in the shape of a partial cylinder jacket, likewise by welding with the outer tube of metal jacket lead 13.

Figure 3:
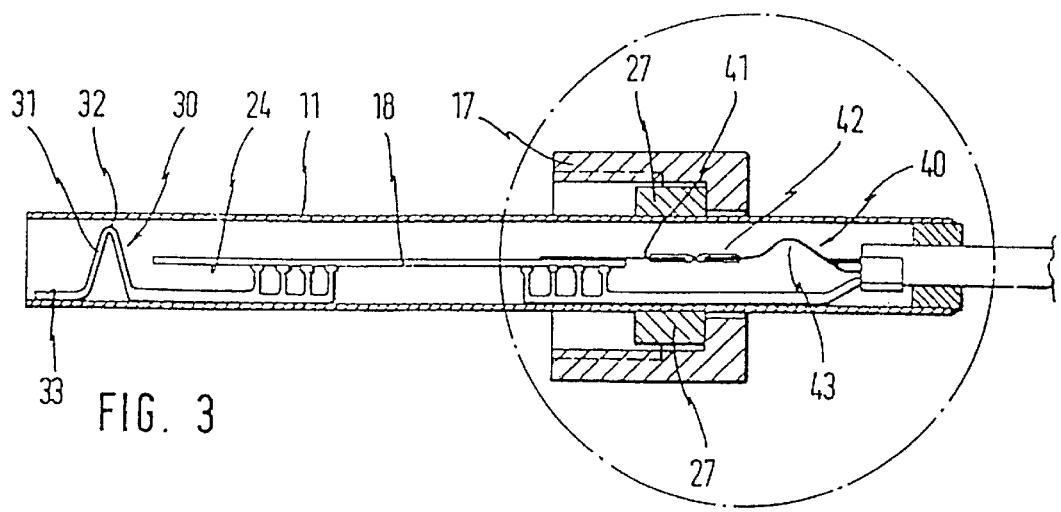
FIG. 3 is a second embodiment of the invention.

Instead of wire knit 20 of the first embodiment in the second embodiment according to FIG. 3, a holding part 30 roughly corresponding to retaining part 21 can be provided in the forward part, said holding part likewise being provided at its end with small legs that likewise run transversely to its length, preferably at right angles, with small feet provided at its end, said feet being connected at metallization 24 with the underside of sensor chip 18 by laser welding. This holding part 30 is provided with a V-shaped bend 31 whose tip 32 is located at a distance from the opposite interior of tube 11. The outermost end 33 of this holding part 30 is secured to the inside of tube 11, for example by welding. The difference in lengthwise thermal expansion between tube 11 and the entire length of sensor chip 18 is compensated by the V-shaped bend 31.

The electrical connection of sensor chip 18 that carries actual sensor element 19 can be provided either by virtue of the fact that either connecting wires 40 of metal jacket lead 13 are welded directly to the sensor chip (FIG. 1) or are connected electrically with one another by means of connecting tabs 41 mounted on sensor chip 18 (FIGS. 3, 4 to 6, and 8) and possibly by a connecting sleeve 42. In both cases the connecting wires are preshaped in such fashion (for example in the form of an arc 43 that serves to relieve tension) and are shaped in the connecting area to the substrate transversely to the length in such fashion that an at least areawise flat support results.

A third, completely preferred embodiment with an electrically conducting clip 50 is shown in FIGS. 4 to 6 (without the housing) and in 8 as a half-open system with supporting support part 20, and has the advantage that the clip has a double function, namely as an electrical connection and as a mechanical holder. The clip has a connecting tab 41 that has a U-shaped bend 54, said tab also being made in the form of a strip, and is mounted by one lengthwise edge of plane sensor chip 18 in such fashion that the two flexible arms 55, 56 of clip 50 rest firmly and flush on both the top and bottom of the sensor chip.

Actual connecting tab 41 begins behind U-shaped bend 54 in the embodiment shown, said tab in turn resting on the surface of sensor chip 18, so that the stiffness of this arrangement is increased. A connecting wire 40 of the internal conductor of metal jacket lead 13 is connected to this connecting tab 41, preferably by laser welding. In the vicinity of U-shaped bend 54 of one clip, the two arms of another clip can be applied laterally, the U-shaped bend of said clip being located on the other side of the sensor chip.

On substrate 53, e.g. $Al_2O_3$ of sensor chip 18, an adhesion-promoting layer 52 is also applied by screen printing and a layer containing platinum is provided on top of this layer, likewise by screen printing, as a contact trace 51. One arm 56 of clip 50 rests on this trace, said arm being welded by laser welding to contact trace 51, as indicated schematically by 57.

We claim:

1. A measuring sensor to be mounted in a measuring opening for measuring a fluid within the measuring opening, comprising:
    a longitudinally extending housing having first and second ends and having an inlet opening at the first end for the fluid to be measured;
    a sensor chip provided in said housing, the sensor chip having a sensor element provided towards the inlet opening and at least one electrically conducting contact provided towards the second end of the housing;
    a lead electrically connected to the at least one electrically conducting contact and extending from the second end of the housing;
    a collar welded to an outside of the housing at a selected position corresponding to a selected installation depth of the opening of the housing into the measuring opening; and
    a threaded connector provided over the collar, wherein the threaded connector mates with a correspondingly threaded element of the measuring opening and secures the sensor in the measuring opening with the selected installation depth by bearing against the collar.

2. A measuring sensor according to claim 1, wherein the collar is laser welded to the housing.

3. A measuring sensor for measuring a fluid, comprising:
    a longitudinally extending housing having first and second ends and having an inlet opening at the first end for the fluid to be measured,
    a sensor chip provided in said housing, the sensor chip having a sensor element provided towards the inlet opening and at least one electrically conducting contact provided towards the second end of the housing;
    a metal jacket lead comprising an outer metal tube, at least one internal conductor, and a mineral material for electrically insulating the at least one conductor, the outer metal tube being laser welded in a fluid-tight manner to the second end of the housing, and the at least one internal conductor being electrically connected to the at least one contact of the sensor chip;
    a collar welded to an outside of the housing at a selected position corresponding to a selected installation depth of the opening of the housing into the measuring opening; and
    a threaded connector provided over the collar, wherein the threaded connector mates with a correspondingly threaded element of the measuring opening and secures the sensor in the measuring opening with the selected installation depth by bearing against the collar.

* * * * *